(12) United States Patent
Dick et al.

(10) Patent No.: US 7,766,481 B2
(45) Date of Patent: Aug. 3, 2010

(54) DEVICE FOR ILLUMINATING ORGANIC OBJECTS

(75) Inventors: Manfred Dick, Gefell (DE); Thomas Mohr, Jena (DE)

(73) Assignee: Carl Zeiss Meditec GmbH, Jena (DE)

( * ) Notice: Subject to any disclaimer, the term of this patent is extended or adjusted under 35 U.S.C. 154(b) by 849 days.

(21) Appl. No.: 11/587,201

(22) PCT Filed: Apr. 22, 2005

(86) PCT No.: PCT/DE2005/000758

§ 371 (c)(1),
(2), (4) Date: Oct. 24, 2006

(87) PCT Pub. No.: WO2005/102148

PCT Pub. Date: Nov. 3, 2005

(65) Prior Publication Data

US 2008/0019127 A1    Jan. 24, 2008

(30) Foreign Application Priority Data

Apr. 24, 2004    (DE) .................. 10 2004 020 663

(51) Int. Cl.
*A61B 3/10* (2006.01)
(52) U.S. Cl. ...................... 351/221; 362/235
(58) Field of Classification Search .............. 351/205, 351/206, 210, 213, 214, 221; 362/227, 235
See application file for complete search history.

(56) References Cited

U.S. PATENT DOCUMENTS

| | | | |
|---|---|---|---|
| 4,213,678 A * | 7/1980 | Pomerantzeff et al. | 351/206 |
| 4,440,477 A * | 4/1984 | Schachar | 351/212 |
| 6,174,749 B1 | 1/2001 | Yuen et al. | |
| 6,179,422 B1 | 1/2001 | Lai | |
| 6,356,088 B1 | 3/2002 | Simon et al. | |
| 6,840,622 B2 | 1/2005 | Kutschbach et al. | |
| 2003/0028115 A1 | 2/2003 | Thomas | |
| 2003/0071970 A1 | 4/2003 | Donnerhacke et al. | |

FOREIGN PATENT DOCUMENTS

| | | |
|---|---|---|
| DE | 298 08 351 U1 | 9/1998 |
| DE | 197 33 195 A1 | 2/1999 |
| DE | 199 59 881 C1 | 10/2001 |

(Continued)

OTHER PUBLICATIONS

A.E. Elsner, "Multiply scattered light tomography," *Lasers and Light*, vol. 8, No. 3, pp. 193-202 (1998).

*Primary Examiner*—Huy K Mai
(74) *Attorney, Agent, or Firm*—Patterson Thuente Christensen Pedersen, P.A.

(57) ABSTRACT

The invention relates to a device for illuminating organic objects, particular organic objects of the eye. Preferably, the device can be used in an opthalmological diagnosis or therapy device. According to the invention, an array of miniaturized light sources is arranged in a spatially defined manner on a plane or a curved surface such that the light sources achieve a packing density that is as high as possible and can be electronically controlled individually in a very quick manner. The light source array is imaged onto the biological object by means of an optical system.

25 Claims, 5 Drawing Sheets

FOREIGN PATENT DOCUMENTS

| | | |
|---|---|---|
| DE | 101 51 314 A1 | 4/2003 |
| EP | 0 485 803 A1 | 5/1992 |
| EP | 0 615 721 A1 | 9/1994 |
| EP | 0 829 933 A2 | 3/1998 |
| EP | 0 905 835 A1 | 3/1999 |
| FR | 2 849 215 | 6/2004 |
| JP | 04125609 A | 4/1992 |
| WO | WO 01/66029 A1 | 9/2001 |
| WO | WO 02/41250 A2 | 5/2002 |

\* cited by examiner

DEVICE FOR ILLUMINATING ORGANIC OBJECTS

FIELD OF THE INVENTION

The invention concerns a device for lighting organic objects, in particular the eye. It is preferred for application in ophthalmologic diagnostic or therapy equipment.

BACKGROUND OF THE INVENTION

In eye medicine, both during diagnosis and therapy, light is frequently used. This can be particularly provided, since the eye is mostly transparent and can be reached by rays of light, practically in its entirety. Hereinafter, light must be understood as the entire visible spectrum from ultraviolet to infrared emissions.

Slit lamps, eye-fundus cameras and laser scan ophthalmoscopes are particularly well known diagnostic devices which work with light.

A slit lamp produces a variable light section by means of a gap picture projection in the eye, with which conclusions may be obtained depending on the condition of the individual media of the eye. Usually the slit images are produced mechanically by means of the width and length of the variable gap. From patent DE 101 51 314, whose entire contents is incorporated by reference, a well-known light section may also be produced by means of an appropriate light distribution from DMDs (digital Mirror devices), LED (Light Emitting Diode), LCD (Liquid Crystal display) or OLEDs (Organic Light Emitting Diodes) for developed micro displays. What all of these light sources have in common is that they permit only a relatively small image frequency, since they show either mechanically moved parts (DMD) or long image retention.

With a fundus camera, such as the one known from patent DE 298 08 351 U1, the eye background is illuminated with a classical light source like a halogen or a mercury vapor lamp and afterwards a photographic or digital image of the retina is produced. It is also widely understood that these photographs can only be taken in certain spectral areas, in order to cause fluorescence of molecules in interest, which is produced by means of appropriate lighting. For special purposes, flash photographs are also taken in order to recognize quickly occurring processes. However additional photo flash lamps are necessary, which must be linked over the appropriate additional optics into the path of rays. Also, these flash lamps have a limited field rate.

With a laser Scan ophthalmoscope, such as the one described in patent DE 198 35 967 C2, the inside of the eye is scanned by means of a 2 or 3 dimensional mechanical scanner with positioned laser beam and arising fluorescence is detected. Because of the mechanical movement of the scanners, the picture recording frequency is limited in this case, so that rapid procedures cannot be pursued, in addition to which geometrical disturbances are produced in the contents of the resulting picture due to the involuntary movements of the eye. Light-based therapy devices are likewise well known in eye medicine. Thus, treatment of visual defects by means of laser radiation removing material from the cornea may be done with equipment such as the one described in patent WO 01/66029, whose complete contents are incorporated by reference. The beam of a treatment laser is guided by means of a mechanical scanner which has moving mirrors, purposefully placed across the treatment area. The mechanics of the scanner are also here the limiting factor for increasing the treatment speed and thus to reduce the treatment time.

The involuntary eye movements, which arise during treatment, lead to deviations between the intended and the actual place of the material removal. The resulting errors can be avoided by using an eye tracker, which detects the momentary position/line of sight of the eye, so that it can recognize these movements. These movements are then taken into account during the control of material removal and thus balanced.

In U.S. Pat. No. 6,179,422, whose entire contents are incorporated by reference, such an eye tracker is described, which for its part leads an IR laser beam quickly across the pupil of the eye and the eye limbus by means of such a scanner. The reflected radiation is detected by means of a fast photodiode and the movement of the eye can be determined from the contrast shifts of the pupil flanks and the eye limbus between individual scans. This solution is also limited by the accuracy and speed of the mechanical scanner.

The invention is also applicable in other procedures for the investigation of biological objects such as confocal microscopy, for example.

From patent EP 485803 B1, all contents of which are incorporated by reference, a con-focal microscope is well known, which uses a LED or a LCD array for lighting the sample and analyzes the lighted sample by means of a detector array. Therefore, this microscope is not suitable for the examination of quick procedures. Also, for example, laser scanning microscopes, known from patent DE 197 33 195 A1, use mechanical scanners to deflect laser beams used for lighting the sample and are, therefore, likewise not suitable for the investigation of very fast procedures. However, only in recent years the interest in the investigation of extremely fast molecular reciprocal effects in biology has substantially risen.

SUMMARY OF THE INVENTION

The purpose of the invention is to circumvent the disadvantages of the state of the art and to provide an extremely fast variable lighting.

According to invention, an array of miniaturized light sources is arranged on a planar or a curved surface in such a spatially defined way that these light sources achieve a component density as high as possible and may be individually controlled electronically in a very fast way. Thereby the individual light sources array can form a regular and closely packed rectangle, as well as an arbitrary one, so that different adapted evaluation forms can take place.

This light source array can be represented by means of an optical system on the biological object.

In case of a diagnostic device or a microscope, the device according to invention includes a detector, which registers and supplies the reflected, scattered or fluorescent radiation portions of the diagnostic object to an evaluation unit, whereby this detector can also detect selected wavelengths, if necessary. The advantage of the invention is that a spatially highly resolved structured lighting can be achieved without any moving parts, very fast and with variable spectra. The eye position can be determined with an eye tracker by fast individual detectors, where the spatial dissolution is already given by the mapped light source array, so the use of image-processing CCD sensors is not necessary.

If the resolution given by the spatial arrangement of the light sources is not sufficient, according to invention this can be adapted in the device by a making a smaller mapping on the object. In a diagnostic device, it is convenient to calibrate the lighting device, for example over a homogeneous object. In a therapy device, the benefit is that the delivered beam is homogenized by means of homogenizing intermediate optics (for example, based on micro-optical elements).

With the possibility of selecting the spatially structured intensity and color/wavelength of the individual light sources, temporarily and spectrally variable intensity profiles can be generated, which can be adapted to different application purposes. It is advantageous, if the lighting device consists of a miniaturized light source array formed by compact light-emitting semiconductor diodes or semiconductor lasers that show an emission divergence as small as possible and has very fast switching times, whose emission intensity is electronically adjustable. A particularly suitable design for the light sources is the Vertical Cavity Surface Emitting Laser (VCSEL), which is described in the book of K. J. Ebeling "Integrated Optoelectronics", Springer Publishers, Berlin 1992. For example, in patent EP 905 835 A1, a two-dimensional array of VCSEL light sources is described, which are individually addressable or controllable. In U.S. Pat. No. 6,174,749 a manufacturing process for producing different wavelengths/colors out of radiating VCSELs is depicted in the book of Connie J. Chag-Hasnain, "Tunable VCSEL", IEEE J. Selected Topics in Quantum Electronics, Volume 6 (2000) No. 6, P. 978 FF which also describes tunable VCSELs.

In order to increase the object lighting homogeneity or structure, the emission profiles of the individual beam sources can be accordingly selected, in order to obtain an intensity profile in the projected overlapping as homogeneous or structured as possible. Gauss-shaped intensity profiles are favorable for homogeneous illumination. An increase of the dissolving power of the device according to invention can be accomplished by a time or intensity dependant modulation of particular and/or neighboring light sources of the light sources array.

BRIEF DESCRIPTION OF THE DRAWINGS

The invention is described in further detail in the following schematic designs.

DETAILED DESCRIPTION

Figure 1:
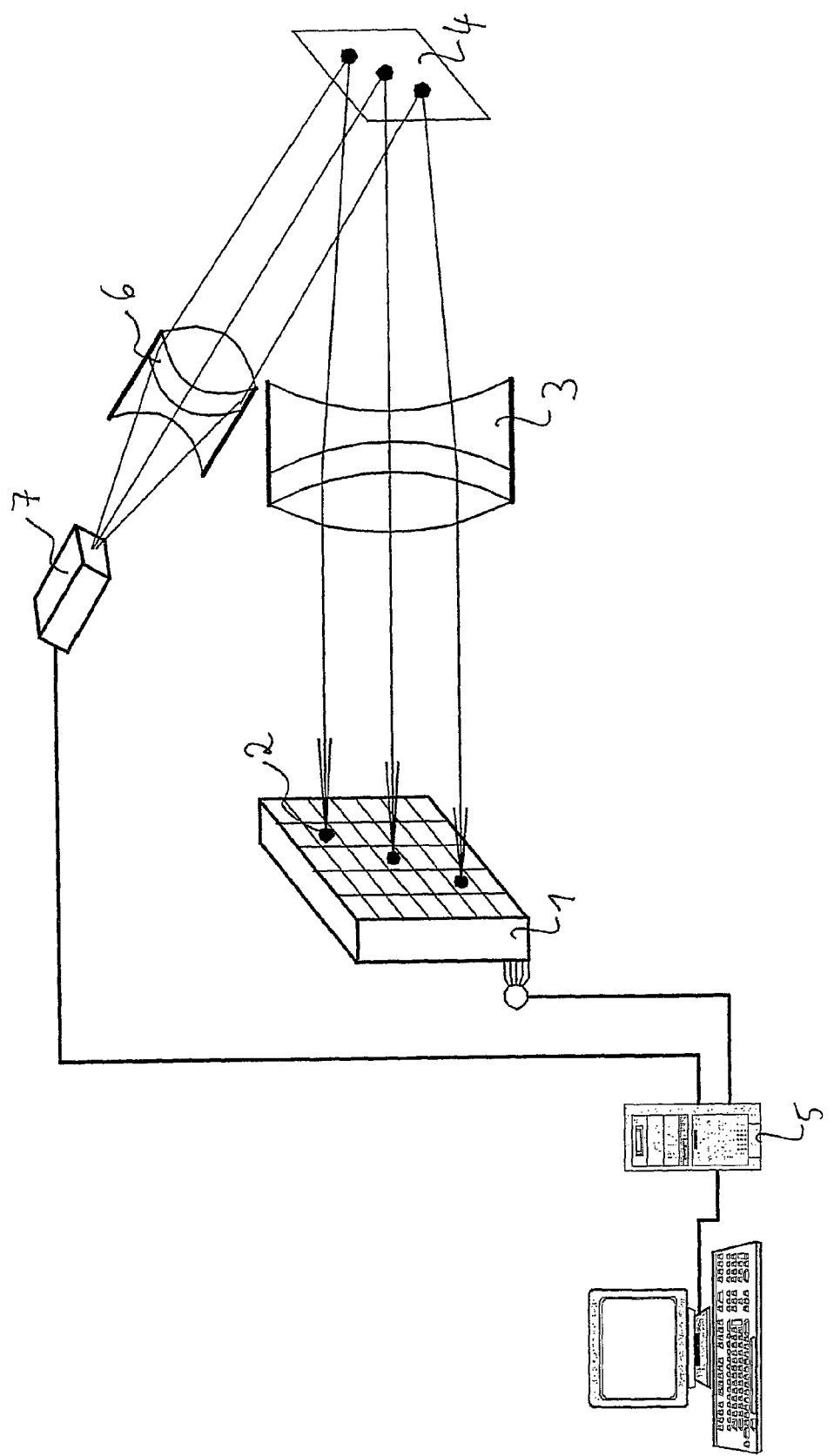
FIG. 1 shows the basic principle of the invention.

In FIG. 1, an array 1 formed by individual light sources 2, which for example can be VCSEL elements arranged in such a way that biological sample 4 is mapped over projection optics 3.

The individual light sources 2 of array 1 can be controlled by means of a computer 5, which can regulate their intensity, color (wavelength) and/or illumination period. The control circuit required for this purpose is not represented here. The outgoing light reflected, scattered, or otherwise emitted from a fluorescent source of the sample will be mapped by means of mapping optics 6 on a detector 7, which is connected to computer 5. The evaluation of the information received from detector 7 can take place then in computer 5 according to the broadly known and intended targeted application adapted procedures.

Figure 2:
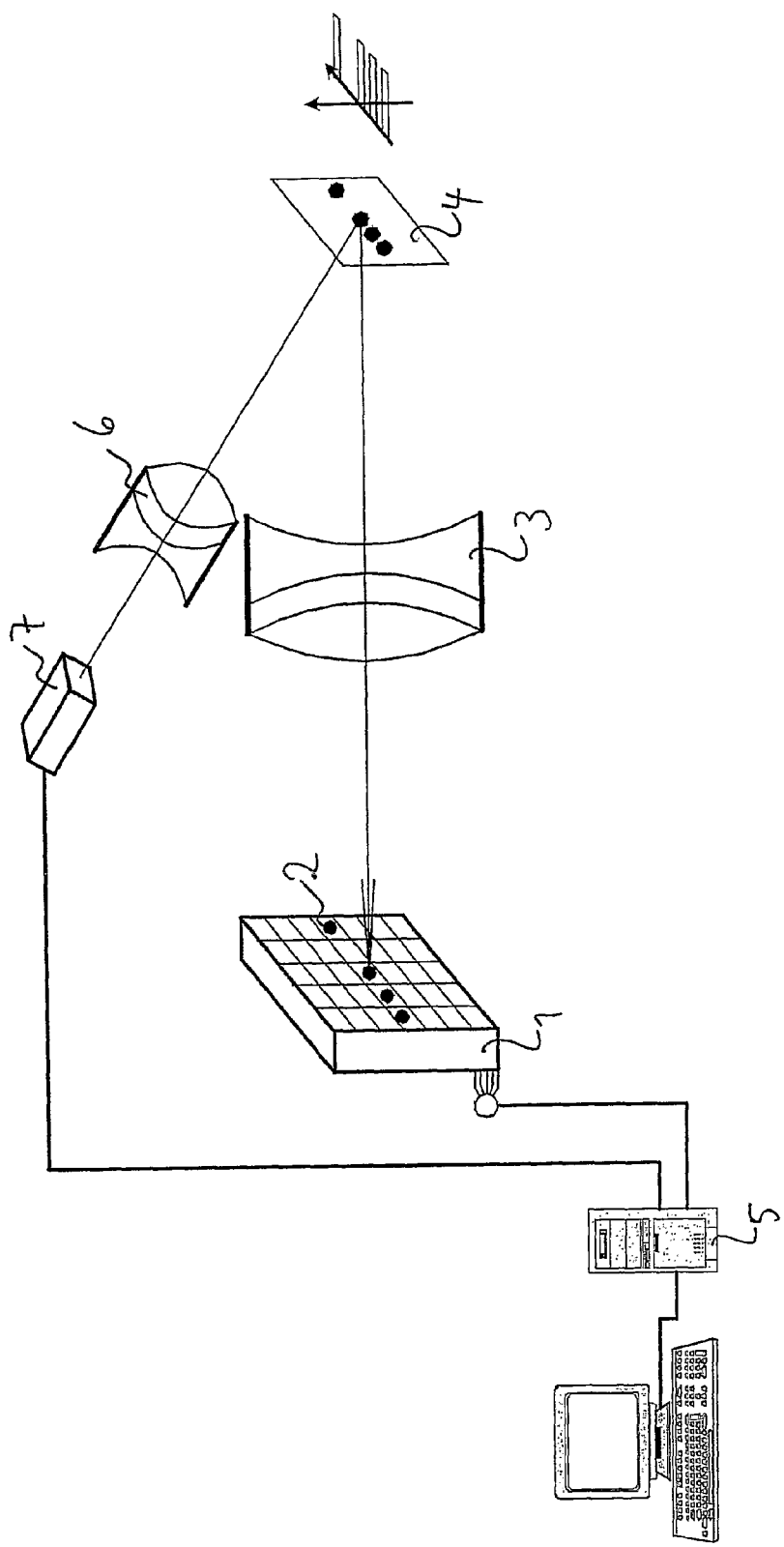
FIG. 2 shows the application of the invention as an ultra fast scanner.
Figure 3:
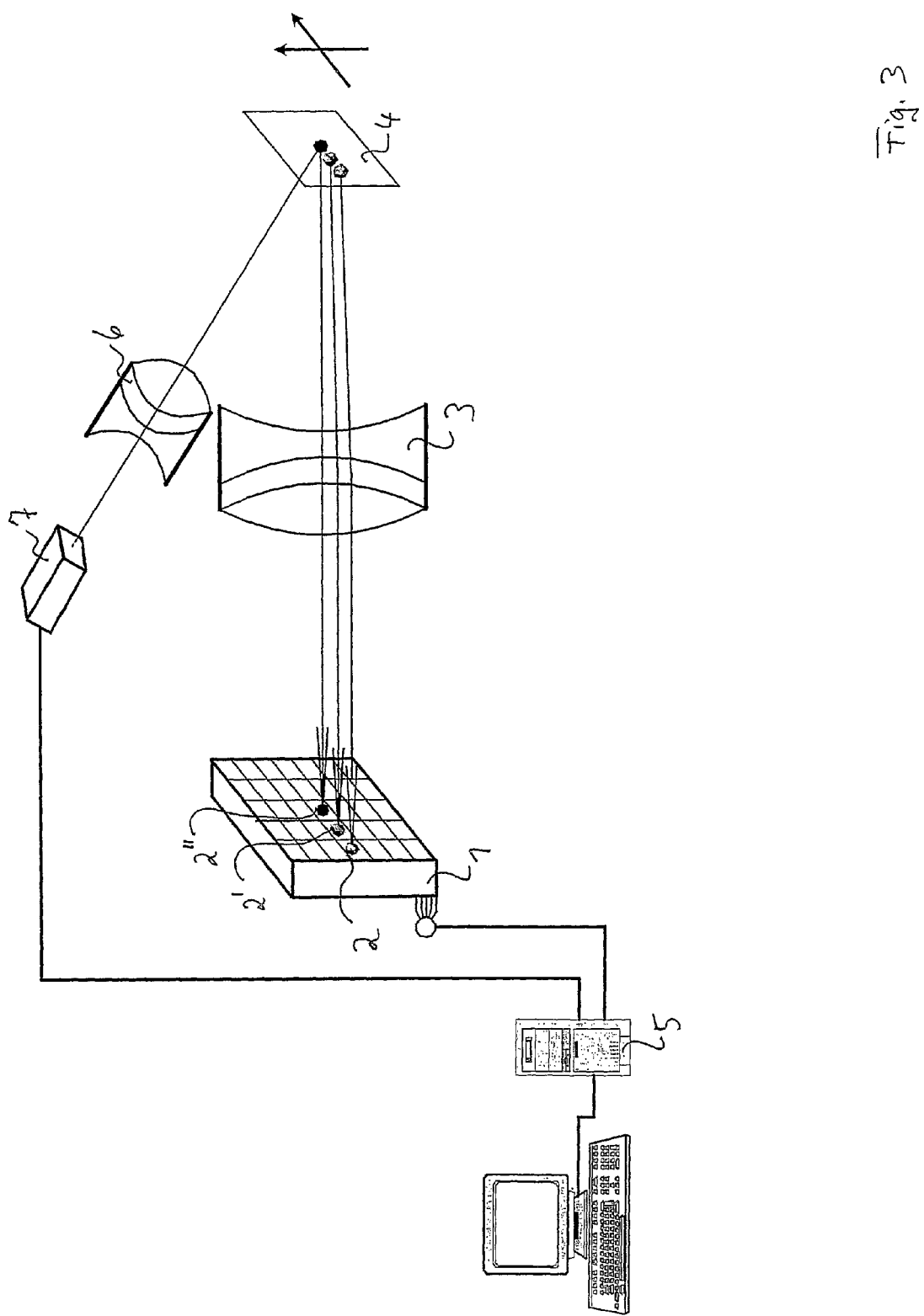
FIG. 3 shows multi-spectral lighting.
Figure 4:
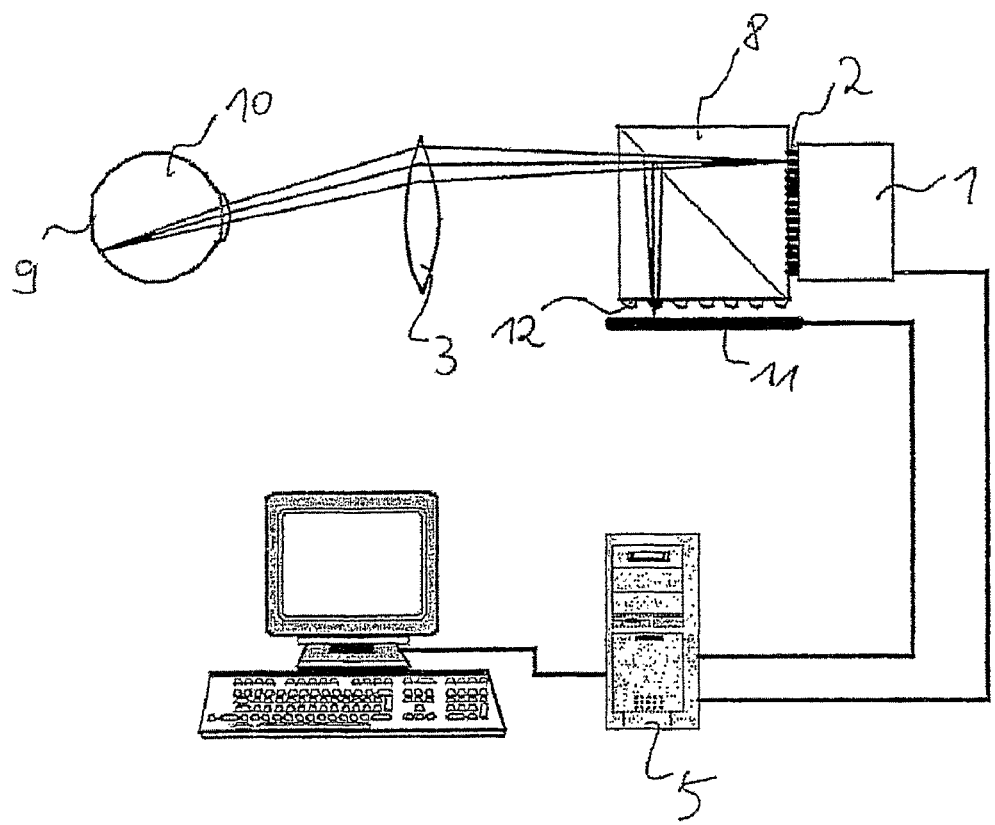
FIG. 4 shows the application form of a co-focal detector.

FIG. 2 shows a series of light sources 2 on array 1 that will be successively switched on and off under control of computer 5, in ultra short time intervals (ranging from a few ns to µs). Using the projection on sample 4, the scanning will take place very fast depending on the sample and will be accomplished without mechanical elements. The light radiated from sample 4 is received by detector 7 and analyzed in computer 5. Such a configuration form can be applied for example as an eye tracker, a digital slit lamp, in the pupilometry or as a scanning fundus camera. Likewise, a laser-scanning microscope can be assembled according to this basic structure. FIG. 3 depicts an application in which the individual light sources 2, 2', 2" of array 1 radiate different wavelengths. In this way, that allows them to detect the wavelength profile of sample 4, as it is used for example in scanning fundus cameras. FIG. 4 shows the application of a device according to invention in con-focal microscopy, in which the scanned laser beam from the light source array and the con-focal detector is replaced by a micro lens array with a coupled receiving chip, a CCD chip (similar to a Shack-Hartmann sensor). The radiation emitted from the x-y-VCSEL array 1 is projected by a 50% dividing mirror (beam splitter cube 8) over the projection optics 3 into the image plane on retina 9 of eye 10. The secondary light sources raster developing there is projected again over the dividing mirror (beam splitter cube 8) on a sensor array 11, for example with a micro lens 12 and electronic evaluation. The sensor array will assume the function of the conventional detector with an aperture in a multiple array configuration. A first configuration form of sensor array 1 can be the spatial structure of the adapted micro lens array of the VCSEL array coupled with a CCD chip. Each individual miniature lens of the micro lens array takes over the function of mapping optics 6. The shutter function of the conventional detector with aperture is carried out, for example, by the fact that the reflected intensity can only be evaluated centrically in each case by the upstream micro lens pixels lying on sensor array 11, which the others do not detect. However, the off center pixels in each case can be used around the grid given by the structure of the device to smooth according to invention. The second configuration form can also use an aperture mask and associated individual receiving diodes, whereby here again the structure and grid to be considered are those from light source array 1.

Each of these configurations can be used also in connection with a microscope for the investigation of biological preparations. In addition, wave front sensor can also be made according to Hartmann-Shack with this configuration and the appropriate evaluation algorithms.

This new con-focal scanning microscope can be implemented in a very compact and durable design without moving parts and can, hence, be applied in a trial application in an eye with lower expenses. Therefore, the scanning function can be explained by the fact that the successively neighboring VCSEL's are switched on and off and thus temporally scanned according to the conventional principle. However, this emulation is not necessary if sensor array 11 possesses an accordingly high evaluation capacity, as the light sources 2 are switched on at the same time and the received signals are evaluated at the same time. The cyclic duration of the optimal reception intensity can be adjusted. Further, extremely fast dynamic procedures can also be examined by the pulsating operation mode of the system.

Figure 5:
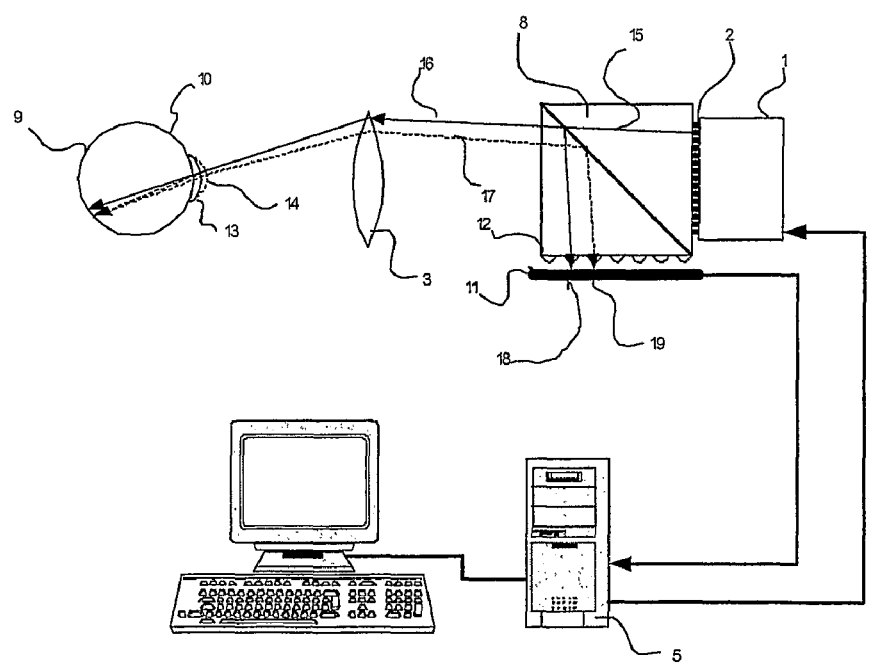
FIG. 5 shows the application form of a refractor.

FIG. 5 depicts the application of the device according to invention in a refractor, whereby the optical structure corresponds to a large extent to the one shown in FIG. 4. The radiation emitted by the x-y-VCSEL array 1 is projected for example by a 50% dividing mirror (beam splitter cube 8) over projection optics 3 on the retina 9 of eye 10. The raster of the secondary light sources developing there is projected again over the dividing mirror (beam splitter cube 8) on a sensor array 11, for example, with micro lenses 12 and the electronic evaluation. Schematically the eyepiece is formed by a normal sighted (emmetropic) eye (reference symbol 13), and are also represented for an eye with defective vision (ametropic) (reference symbol 14). A ray of light 16 emitted from VCSEL array 1 gets to different locations on Retina 9 through the different openings in eye-part 13 and/or 14. The reflection at retina 9 leads in the case of the normal sighted eye to the reflected ray 16, which is directed by the dividing mirror of the dividing cube 8 on sensor element 18 of sensor array 11. For the eye with defective vision, there follows reflection into ray 17, which meets another sensor element, sensor element 19. Thereby the mapping behavior of eye 10 can be determined from the different places impacted by the reflected ray at sensor array 11, which is detected electronically and conveyed to computer 5.

Figure 6:
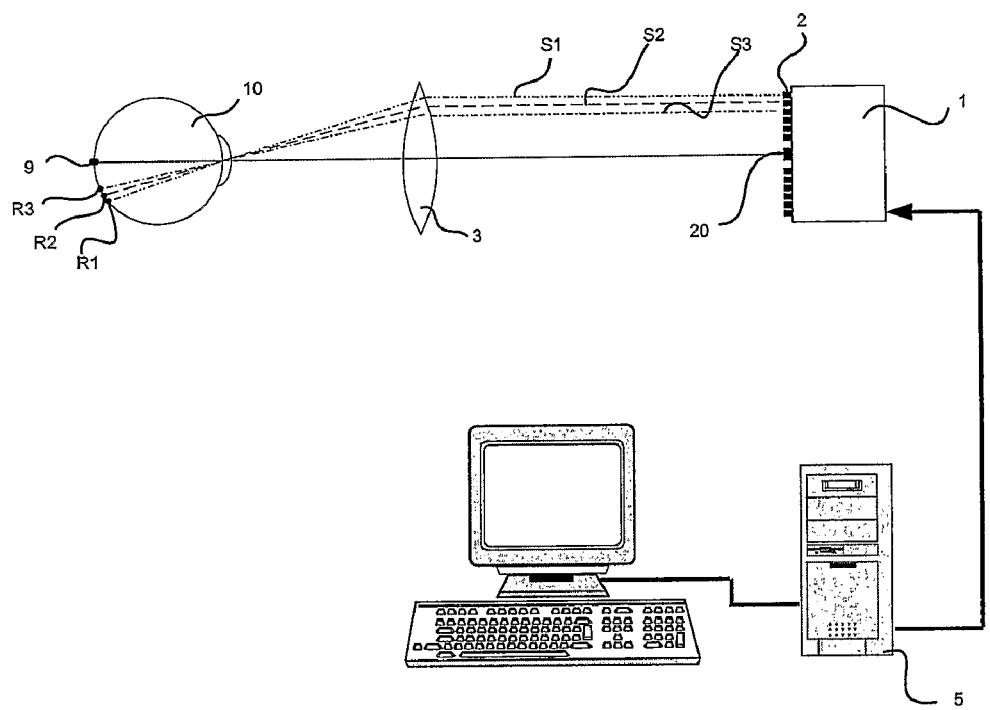
FIG. 6 shows the application form of a perimeter.

FIG. 6 shows a device according to the invention to determine the visual field of a patient.

The radiation emitted from the x-y-VCSEL array 1 is projected over projection optics 3 on Retina 9 of an eye 10, whereby rays S1, S2, S3 of different elements from the VCSEL array 1 strike different locations R1, R2, R3 of retina 9. An additionally existing target 20, which for instance can be a yellow LED or a specific sample represented by the VCSEL array 1, serves for the eye adjustment. The sensory impression caused by the impact of rays S1, S2, S3 over the Retina can then be determined subjectively in a well-known way, either by the interaction of the patient or objectively by evaluating the nerve impulses to the brain stream. Appropriate configurations and evaluation procedures are indicated for example in patent documents DE 198 55 848, DE 199 61 323, DE 101 40 871 and DE 101 46 330, whose entire contents is incorporated by reference.

Figure 7:
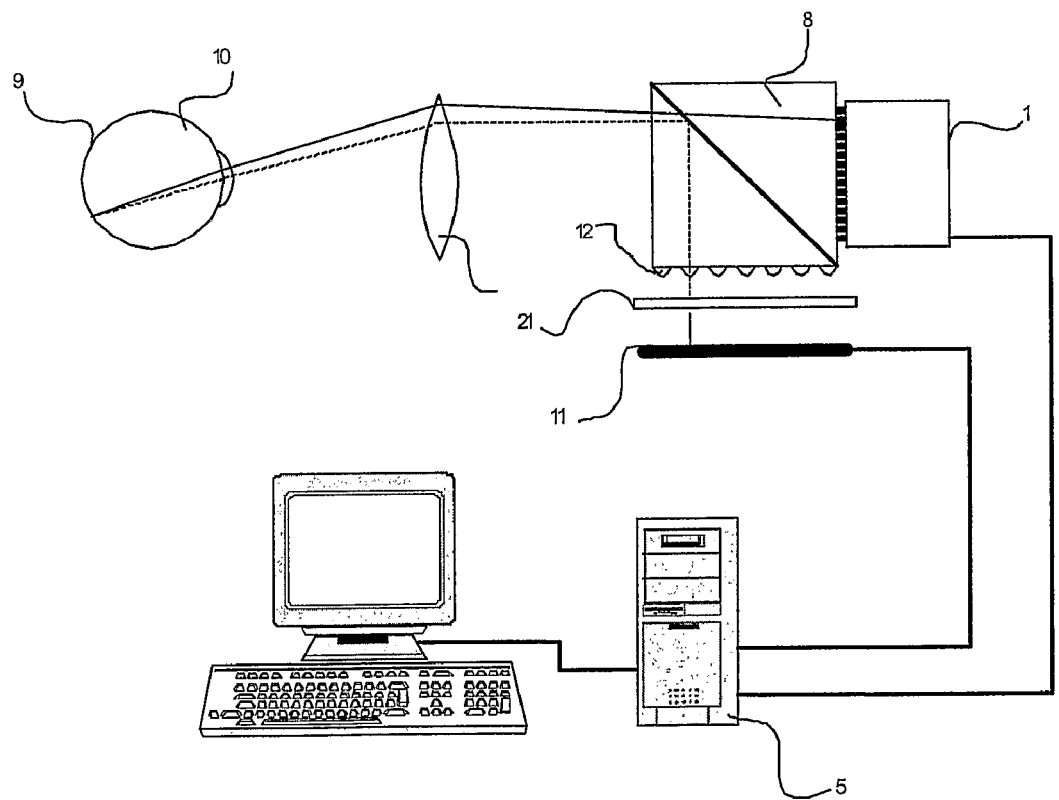
FIG. 7 shows the application form of a fluorescent camera.

FIG. 7 shows a device according to the invention in a fluorescent camera. The radiation emitted from the x-y-VCSEL-array 1 with a certain excitation wavelength $\lambda_1$ is projected for instance by a 50% dividing mirror (beam splitter cube 8) over projection optics 3 on the retina 9 of an eye 10 and the tissue found there is stimulated by means of an inserted fluorescent dye with a fluorescence wavelength $\lambda_2$. The fluorescent light that arrives over the beam splitter 8 to the receiver 11 is coupled with computer 5. In order to prevent the stimulating light from reaching the receiver, a band elimination filter 21 is connected upstream for wavelength $\lambda_1$. For example, the tissue characteristics can be detected reliably by evaluating the local distribution of the fluorescent light. If the VCSEL array 1 according with the application example shown in FIG. 2 can emit several wavelengths, it can also stimulate and detect the different corresponding fluorescences. The cornea or the eyepiece can be spectrally examined in the same way with the device according to invention.

Therefore, each light source can be assigned a directly neighboring detector for monitoring the intensity and/or color, as is described in patent EP 829 933 A2.

In the context of this representation and the device according to invention, all diode lasers can be understood by the concept of a VCSEL light source, whose radiation direction lies perpendicularly to the surface of the array or their active zone. It can thereby concern, in particular, also around NECSEL (Novalux extended cavity surface emitting lasers) or diode lasers, whose resonator lies essentially parallel to the active zone, and are provided with a bending or reflecting structure, which uncouples laser radiation perpendicularly from the array or from the active zone.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. A device for illuminating organic objects, comprising:
a controllable light source; and
mapping optics, in which the controllable light source comprises a plurality of individual light sources, whose intensity and/or color can be changed with a frequency greater than about 100 cycles per second.

2. A device for lighting organic objects according to claim 1, in which the frequency is greater than about 1000 cycles per second.

3. A device for lighting organic objects according to claim 1, in which the frequency is greater than about 10,000 cycles per second.

4. A device for lighting organic objects according to claim 1, in which the frequency is greater than about 100,000 cycles per second.

5. A device for lighting organic objects according to claim 1, in which the frequency is greater than about 1,000,000 cycles per second.

6. A device for lighting organic objects according to claim 1, in which the frequency is greater than about 10,000,000 cycles per second.

7. A device for lighting organic objects according to claim 1, in which the individual light sources are arranged in a regular one or two dimensional array.

8. A device for lighting organic objects according to claim 1, in which the individual light sources are arranged in a substantially planar array.

9. A device for lighting organic objects according to claim 1, in which the individual light sources are arranged in a curved array.

10. A device for lighting organic objects according to claim 1, in which light returned from the organic object is received by at least one detector.

11. A device for lighting organic objects according to claim 10, in which the light received by the detector is analyzed spatially, temporally and/or spectrally.

12. A device for lighting organic objects according to claim 10, in which the individual light sources comprise light-emitting semiconductor diodes or semiconductor lasers, whose intensity and/or color are controllable electronically.

13. A device for lighting organic objects according to claim 10, in which the light sources are arranged before one or more micro-optical elements.

14. A device for lighting organic objects according to claim 10, in which at least one of the light sources further comprises a detector for monitoring the intensity and/or color of the light source.

15. An opthalmologic diagnostic unit, comprising at least one device for lighting organic objects according to claim 1.

16. Opthalmologic therapy equipment comprising at least one device for lighting organic objects according to claim 1.

17. A confocal microscope comprising at least one device for lighting organic objects according to claim 1.

18. A slit lamp, comprising at least one device for lighting organic objects according to claim 1.

19. A fundus camera, comprising at least one device for lighting organic objects according to claim 1.

20. A laser opthalmoscope, comprising at least one device for lighting organic objects according to claim 1.

21. An eye tracker, comprising at least one device for lighting organic objects according to claim 1.

22. Wave front sensor, comprising at least one device for lighting organic objects according to claim 1.

23. A Shack-Hartmann type wave front sensor, comprising at least one device for lighting organic objects according to claim 1.

24. A refractometer, comprising at least one device for lighting organic objects according to claim 1.

25. A perimeter, comprising at least one device for lighting organic objects according to claim 1.

* * * * *

UNITED STATES PATENT AND TRADEMARK OFFICE
CERTIFICATE OF CORRECTION

| | | |
|---|---|---|
| PATENT NO. | : 7,766,481 B2 | Page 1 of 1 |
| APPLICATION NO. | : 11/587201 | |
| DATED | : August 3, 2010 | |
| INVENTOR(S) | : Manfred Dick and Thomas Mohr | |

It is certified that error appears in the above-identified patent and that said Letters Patent is hereby corrected as shown below:

On the title page, item (73) Assignee: change "Carl Zeiss Meditec GmbH" to read as
--Carl Zeiss Meditec AG--.

Column 2, line 64, change "... be adapted in the device by a making a smaller mapping" to read as
--... be adapted in the device by making a smaller mapping--.

Signed and Sealed this
Fourth Day of September, 2012

David J. Kappos
*Director of the United States Patent and Trademark Office*